United States Patent [19]

Paugh et al.

[11] 4,026,022

[45] May 31, 1977

[54] ORTHODONTIC APPLIANCE

[75] Inventors: Edward C. Paugh, Hacienda Heights; Dan Q. Broughton, Laverne, both of Calif.

[73] Assignee: Ormco Corporation, Glendora, Calif.

[22] Filed: Oct. 14, 1975

[21] Appl. No.: 622,000

Related U.S. Application Data

[62] Division of Ser. No. 537,479, Dec. 30, 1974, abandoned.

[52] U.S. Cl. ............................................. 32/14 A
[51] Int. Cl.² ........................................ A61C 7/00
[58] Field of Search ................................. 32/14 A

[56] References Cited

UNITED STATES PATENTS

| | | | |
|---|---|---|---|
| 2,196,516 | 4/1940 | Atkinson | 32/14 A |
| 2,257,069 | 9/1941 | Peak | 32/14 A |
| 3,085,336 | 4/1963 | Kesling | 32/14 A |
| 3,163,933 | 1/1965 | Begg et al. | 32/14 A |
| 3,178,821 | 4/1965 | Kesling | 32/14 A |
| 3,408,739 | 11/1968 | Johnson | 32/14 A |
| 3,435,527 | 4/1969 | Kesling | 32/14 A |
| 3,445,933 | 5/1969 | Kesling | 32/14 A |
| 3,574,940 | 4/1971 | Allesee | 32/14 A |

*Primary Examiner*—Robert Peshock
*Attorney, Agent, or Firm*—Jessup & Beecher

[57] ABSTRACT

An orthodontic appliance adapted to be secured to a tooth by any suitable means, such as a tooth band or by direct bonding. The appliance consists of a bracket and a lock pin which holds an arch wire to the bracket in any of a plurality of attitudes to accommodate successive phases in orthodontic treatment. The offset head of the lock pin engages the gingival edge of the bracket to define the limits of the arch-wire-receiving slot on a gingival-occlusal axis. A notch in the edge inhibits the pin from moving laterally or rotating in the bracket. The bracket is formed by embossing a sheet of material to form a pin-receiving channel. Tabs are bent inwardly from the channel side walls to provide fulcrum edge means approximating a knife edge, on which the arch wire bears as it passes through the bracket.

8 Claims, 21 Drawing Figures

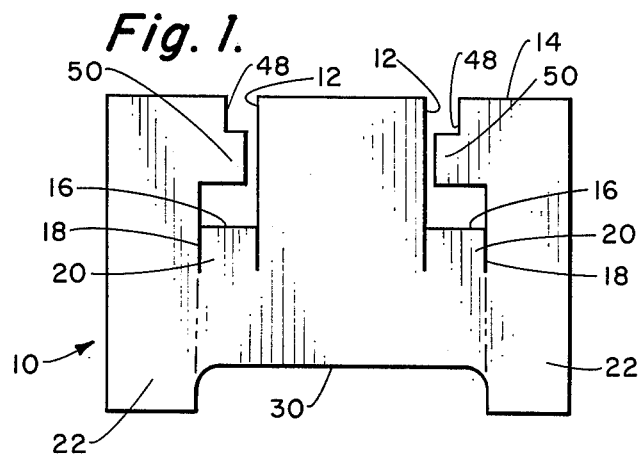
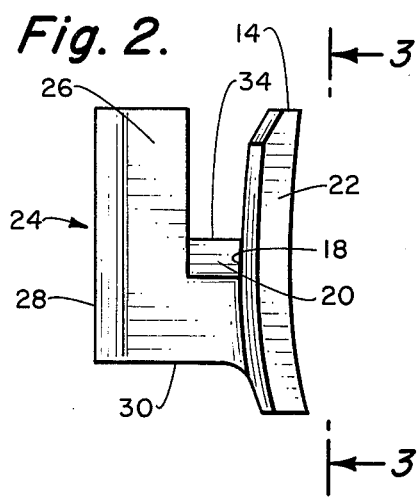
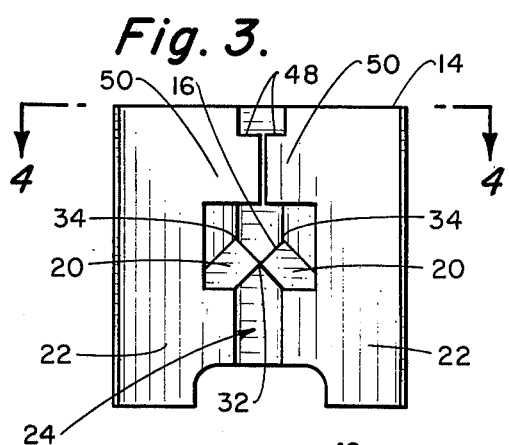
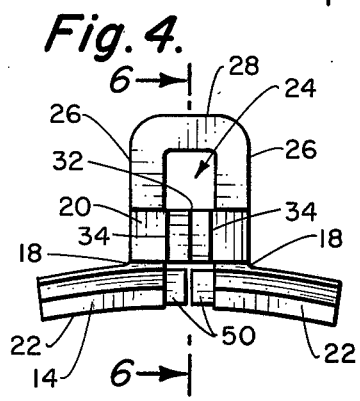
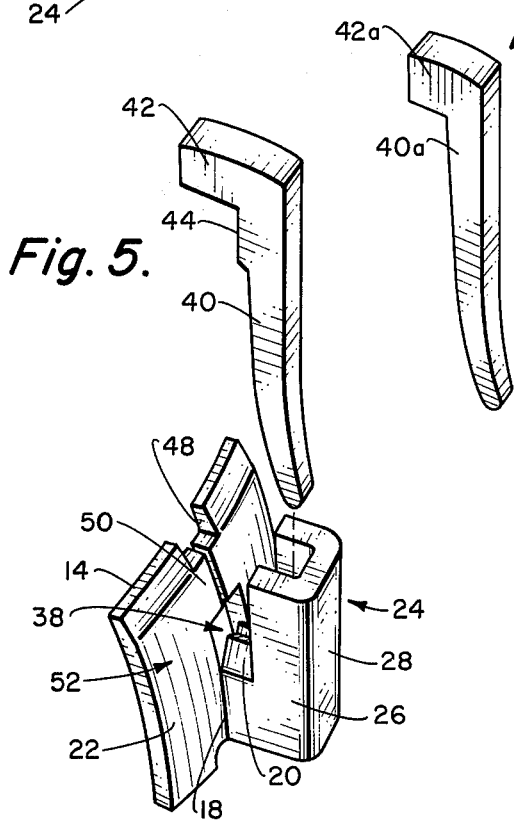
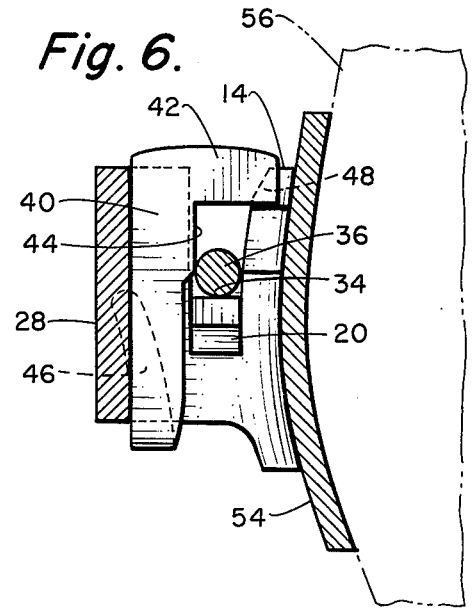

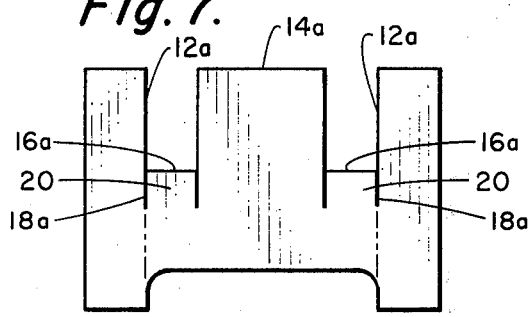
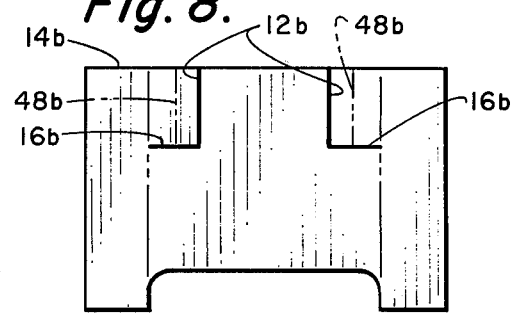
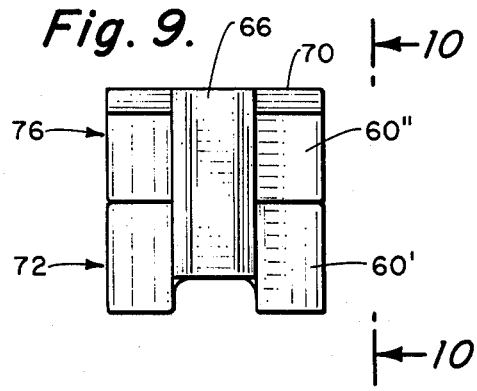
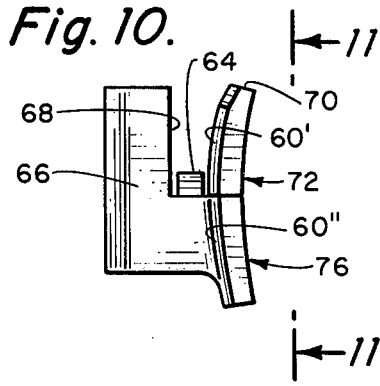
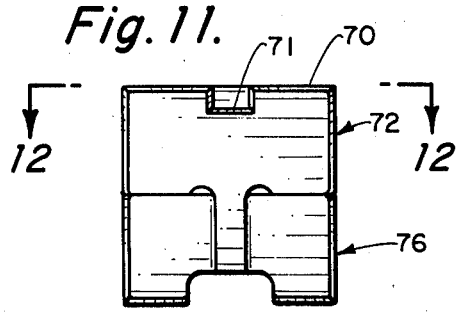
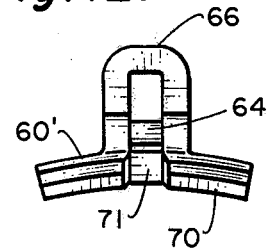
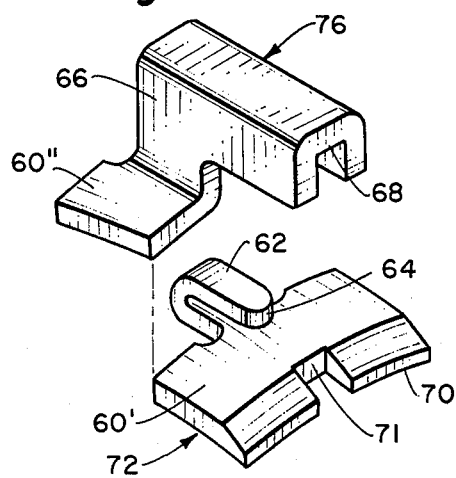
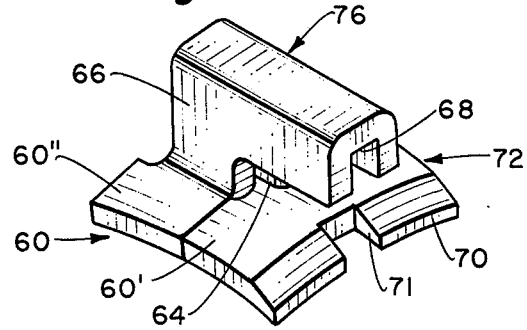

ORTHODONTIC APPLIANCE

This is division of application Ser. No. 537,479, filed Dec. 30, 1974 and now abandoned.

DESCRIPTION OF THE FIGURES

FIGS. 1 through 6 show a preferred form of the invention.

FIG. 1 is a view of a blank or sheet of material from which a preferred form of the bracket is formed.

FIG. 2 is a side view of the bracket formed from the blank of FIG. 1.

FIG. 3 is a rear view of the bracket, looking in a labial direction, and taken on line 3—3 in FIG. 2.

FIG. 4 is a gingival view of the bracket, taken on line 4—4 in FIG. 3.

FIG. 5 is a perspective view of the bracket showing a first-phase lock pin about to be inserted in the bracket channel.

FIG 5A shows a lock pin used in a later phase of treatment.

FIG. 6 is an elevational cross-section showing the lock pin holding an arch wire in place.

FIG. 7 shows a blank or sheet from which a second form of the invention may be formed.

FIG. 8 shows a sheet blank from which a third form of the invention may be formed.

FIGS. 9 through 14 show a fourth form of the invention.

FIG. 9 is an elevation of the bracket looking in a lingual direction.

FIG. 10 is a side view of the bracket taken on line 10—10 in FIG. 9.

FIG. 11 is a rear view of the bracket taken on line 11—11 in FIG. 10.

FIG. 12 is a gingival view of the bracket, taken on line 12—12 in FIG. 11.

FIG. 13 is an exploded perspective view showing the two parts of the bracket before assembly.

FIG. 14 is a perspective view showing the assembled bracket.

FIG. 15 is an elevational view looking in a lingual direction.

FIG. 16 is a side view taken on line 16—16 in FIG. 15.

FIG. 17 is an elevational view taken on line 17—17 in FIG. 16.

FIG. 18 is an end view taken on line 18—18 in FIG. 17, and looking along the gingival-occlusal axis.

FIG. 19 is an exploded perspective view showing the two parts of the bracket before assembly.

FIG. 20 is a perspective view showing the assembled bracket.

DETAILED DESCRIPTION OF THE EMBODIMENT OF THE INVENTION

Figure 15:
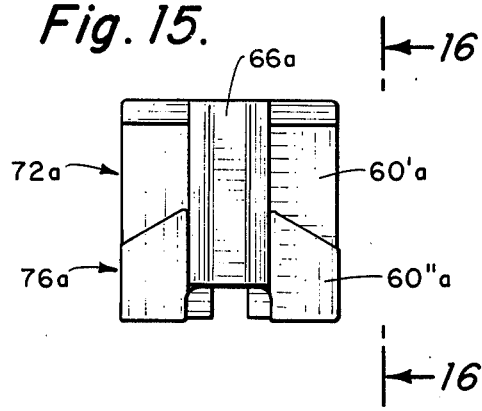
FIGS. 15 through 20 show a fifth form of the invention.
Figure 16:
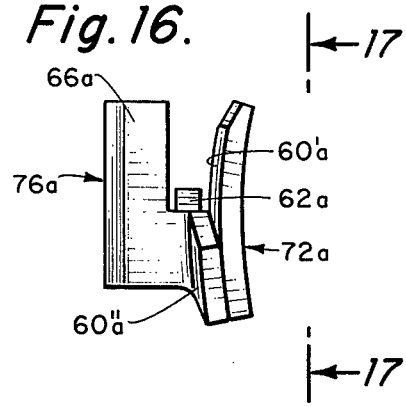
Figure 17:
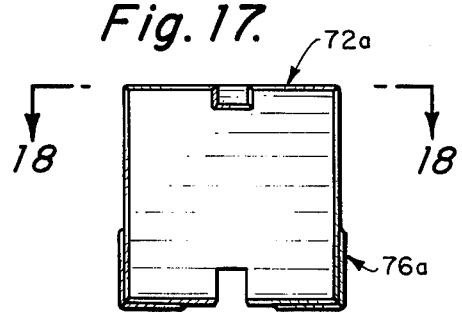
Figure 18:
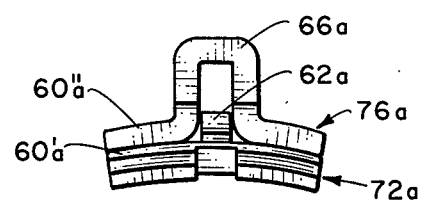
Figure 19:
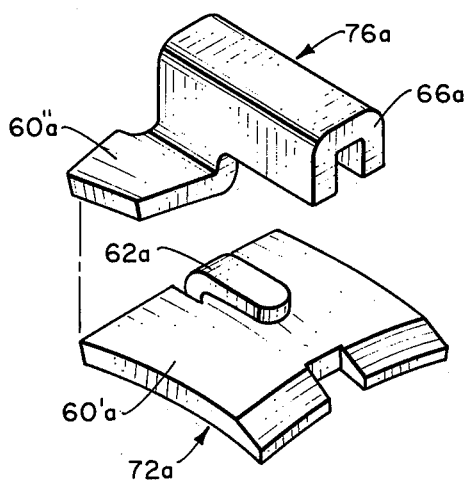

FIGS. 1 through 6 of the drawings show a preferred form of the present invention, consisting of a generally flat blank 10 of substantially rigid yet bendable material, such as stainless steel. The sheet 10 is pierced along a pair of parallel first lines 12 extending substantially perpendicularly from the gingival edge 14 of the sheet 10. In FIG. 1, the piercing at 12 involves the removal of material, but it may consist of a simple shear or slit without significant removal of material, as shown at 12b in FIG. 8, to be described hereinafter. The sheet 10 is further pierced along aligned second lines 16 extending outward perpendicularly from the slits 12. Here again the piercing may involve the removal of material as shown in FIG. 1, or it may be a simple slitting without significant removal of material, as shown at 16b in FIG. 8. The sheet 10 is further pierced along a pair of third lines 18, parallel to the first lines or slits 12, and located at the outer ends of the second slits 16. The inner ends of the slits 12 and 18, together with the slits 16, form in conjunction a pair of fulcrum tabs 20.

Sheet blank 10 is embossed outwardly along the slit lines 18, as shown in FIG. 4, to form a pair of flange sections 22 with a channel 24 therebetween. The channel 24 has a pair of side walls 26 which are substantially perpendicular to the gingival edge 14 and joined by a center section 28 which completes the formation of the channel 24. The channel 24 is foreshortened at the occlusal end to minimize inconvenience to the wearer, by recessing the occlusal edge of the sheet, as shown at 30 in FIGS. 1 and 2. The recessing at 30 terminates substantially at the bend lines 18, in order to leave as much bearing area as possible for the flanges 22 in their securement to the tooth or tooth band.

The sheet 10, in addition to being embossed to form the channel 24, as shown in FIG. 4, also has the tabs 20 bent obliquely into the channel 24, with the free ends in close proximity, as shown at 32 in FIG. 3, to form fulcrum edge means in the form of closely adjacent fulcrum edges 34 upon which an arch were 36 bears, as shown in FIG. 6. Ideally, the inner facing edges 32 of the tabs 20 could be bevelled to bring the edges 34 flush together, but this would add considerable cost to the product, and it has been found in practice that it is not necessary for a satisfactory product. The reason for bringing the fulcrum edges 34 as close together as is commercially feasible is to minimize the width of the fulcrum on which the arch wire 36 bears in its securement to the bracket. The open region above the tabs 20 in FIG. 5 constitutes a notch 38 for receiving the arch wire 36.

In the use of the bracket shown in FIG. 5 the orthodontist typically employs three phases. In the first two phases a relatively small diameter arch wire 36 is used, and it is desirable to permit movement, within limits, along a gingival-occlusal axis, while closely restricting movement along a lingual-labial axis. To this end the lock pin 40 which is used with the bracket (FIG. 5) has an offset head 42 which, when engaged in the channel 24, bears on the gingival edge 14 to confine the arch wire 36 on a gingival-occlusal axis between the fulcrum edge means 34 and the underside of the head 42. At the same time the arch wire 36 is closely confined on a lingual-labial axis by enlarging he elongate body of the pin 40 immediately under the head 42 to provide a shoulder 44, which closely engages the arch wire 36 and prevents movement in that direction, as shown in FIG. 6. In conventional fashion the pin 40, after being passed into the channel 24, is locked therein by having the tail bent around through substantially 180°, as shown by the dotted line 46 in FIG. 6.

In the third phase of orthodontic treatment the relatively small arc wire 36 is replaced with a larger arch wire wich substantially completely fills the notch 38 in the bracket. It is preferable to lock this arch wire firmly in the notch 38 with substantially no play. To this end the lock pin 40 shown in FIG. 5 is replaced by a lock pin 40a (FIG 5A), which does not have the shoulder 44, and in which the offset head 42a is shortened so that it stops short of the gingival edge 14 and seats itself directly on the larger arch wire.

In order to restrict shifting of the lock pin 40 in the channel 24, a notch 48 is provided in the gingival edge 14 of the bracket, opposite the head 42, and the head resides in this notch 48 as shown in FIG. 6. This not only substantially prevents rotation of the pin 40 in the channel 24, but also inhibits lateral movement of the pin 40 on a mesial-distal axis.

It will be noted that in FIG. 1 the piercing or slit 16 is quite wide and involves the removal of considerable material from the sheet. This is a fabrication technique in that it has been found simpler to stamp out and remove a section of the sheet than to merely pierce a tiny slit 16. In similar vein the central portion of the slit 12 has a small portion of the metal removed because of manufacturing facility. There is left, however, a substantial portion of the sheet parts shown at 50 between the gingival edge 14 and the slit 16, and these parts 50, together with flange sections 22, form a base 52 for the bracket as shown in FIG. 5. When the blank sheet 10 is embossed to form the channel 24, the base wall parts 50 are brought into close adjacency, as best shown in FIGS. 4 and 5, so as to form a substantially continuous gingival edge 14, on which the offset head 42 of the lock pin 40 bears as it is clamped into the bracket, as shown in FIG. 6.

Although the base 52 of the bracket formed by the parts 22 and 50 remains substantially planar after the embossing shown in FIG. 5, it is preferably also formed with a slight curvature in both a gingival-occlusal and a mesial-distal direction. This is done in order to conform to the typical curvature of a tooth band 54, secured around the patient's tooth 56. Alternatively, if desired, the bracket may be secured to the tooth 56 by direct bonding It is preferred to leave a substantial portion of the two base parts 50 integrally joined with the flange sections 22, in order to provide a substantially continuous gingival edge 14, when the sheet 10 is formed into the three-dimensional bracket shown in FIG. 5. However, certain advantages of the invention are possible even though that portion of the sheet 10 is completely removed. This is shown in FIG. 7 where all of the material between the pierce line 16a and the gingival edge 14a is removed. The blank sheet of FIG. 7, while not having the continuous gingival edge, still provides the tabs 20 which may be bent obliquely inward to form the fulcrum edge means 34 for the arch wire 36.

In similar vein, as intimated hereinbefore, it is not necessary to employ the inwardly bent tab feature in order to have the continuous gingival edge feature. This is shown in FIG. 8 where the slits 12b are foreshortened, and at their respective ends the perpendicularly outward slits 16b are formed. The slits 18 of FIG. 1 are omitted. It is thus seen that the blank of FIG. 8 results in a bracket which has a continuous gingival edge 14b, but does not have the closely spaced tabs 20 to provide the sharp knife-blade-like fulcrum 34 for the arch wire 36. The gingival edge 14b may, if desired, be notched, as shown at 48b.

Another form of the invention is shown in FIGS. 9 through 14, wherein the bracket has a generally planar base shown at 60 in FIG. 14. A tab 62 (FIG. 13) extends above the surface of the base and has a pointed free end 64. The end may be rounded as shown in FIG. 13 or may come to a sharp point, depending on the degree of manufacturing care which one wishes to apply. In practice it has been found that the point need not be particularly sharp in order to provide a sufficiently narrow fulcrum for the arch wire. A channel member 66 overlies the tab 62. The gingival end of the channel 66 is relieved at 68 (FIG. 14) to form a notch for receiving an arch wire which bears on the free end 64 of the tab 62.

As in the foregoing embodiments, the gingival edge 70 of the base 60 may be notched at 71 to accommodate the extended offset head 42 of the elongate lock pin 40 (Note FIG. 5).

The bracket shown in FIGS. 9 through 14 is preferably formed in two parts 72 and 76. The first part or member 72 has the tab 62 formed integrally with its base 60'. In the initial stamping of the member 72 the tab 62 extends outwardly from the base 60' and is then bent back through a 180° bend (FIG. 13) to bring the free end 64 into proper position inside the channel member 66. The bracket is completed by formation of the second member 76, which has the channel 66 and the base 60'', which is coplanar with the base 60' of the member 72. The two bases 60' and 60'' may be edge welded together, or may alternatively be left as separate pieces, secured in their operative continguous relationship by being secured to the tooth band 54.

Figure 20:
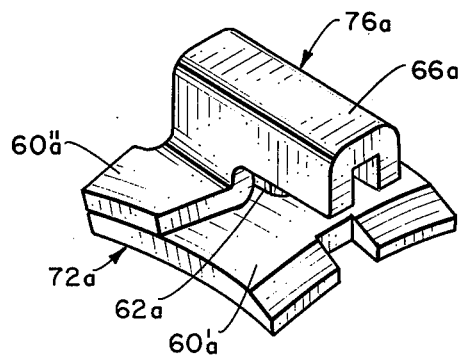

The form of the invention shown in FIGS. 15 through 20 is similar to that shown in FIGS. 9 through 14, except that the base 60a' of the member 72a is of greater extent and underlies the base 60a'' of the second member 76a. As in the form shown in FIG. 13, the tab 62a is initially formed by extending outwardly from the base 60a and is then bent back 180° to overlie the base 60a' and reside in the channel 66a. As shown in FIG. 20, this form of the invention involves face-to-face securement between the bases 60a' and 60a'' as by spot welding.

While most orthodontists prefer to mount the bracket with the arch wire 36 on the gingival side, the bracket may be employed with the edge 14 on the oculusal side.

Whereas the present invention has been shown and described herein in what is conceived to be the best mode contemplated, it is recognized that departures may be made therefrom within the scope of the invention which is therefore not to be limited to the details disclosed herein, but is to be afforded the full scope of the invention.

What is claimed is:

1. An orthodontic bracket comprising:
   a generally planar base;
   a tab extending above the surface of said base and having a pointed free end;
   said tab, when initially formed, extends out from said base and is then bent back through a 180° bend; and
   a channel member overlying said tab and having a portion spaced from said base to provide a notch for receiving an arch wire resting on said end.

2. Bracket in accordance with claim 1 wherein:
   said tab is formed integrally with said base and is bent into position thereabove.

3. Bracket in accordance with claim 1 wherein:
   said base is formed from a first member,
   and said channel is formed from a second member and bonded to said first member.

4. Bracket in accordance with claim 1 wherein:
   said base is formed from a first member, said channel is formed from a second member, and means for securing said members in adjacency to constitute the completed bracket.

5. An orthodontic bracket formed from an initially flat sheet of substantially rigid yet bendable material, said sheet being pierced along a pair of parallel first lines extending substantially perpendicularly from a gingival edge of said sheet;

said sheet being further pierced along aligned second lines extending outward perpendicularly from respective said parallel first lines;

said sheet being further pierced along a pair of third lines parallel to said first lines and located at the respective outer ends of said second lines, and forming in conjunction with said first and second lines, a pair of fulcrum tabs;

said sheet being embossed outwardly along said third lines to form.

a pair of flange sections and a channel therebetween, said channel having side walls substantially perpendicular to said edge, said tabs being bent obliquely into said channel with their free ends in close proximity to form fulcrum edge means for an arch wire secured to the bracket.

6. Bracket in accordance with claim 5 wherein:
the occlusal edge of said sheet opposite said gingival edge is recessed in the area substantially bounded by said lines.

7. Orthodontic bracket in accordance with claim 5 wherein:
substantial portions of the two parts of said sheet lying between said gingival edge and the respective said aligned second lines are left integrally joined with said flange sections, and are brought into adjacency by the embossing of said channel to form a substantially continuous gingival edge for the finished bracket.

8. Bracket in accordance with claim 5 wherein:
the two parts of said sheet lying between said gingival edge and the respective said lines are removed.

* * * * *